United States Patent [19]

Muchel et al.

[11] 4,248,505
[45] Feb. 3, 1981

[54] OPHTHALMOLOGICAL INSTRUMENT

[75] Inventors: Franz Muchel, Königsbronn; Gunther Sümmerer, Oberkochen; Ekkehard Stern, Königsbronn, all of Fed. Rep. of Germany

[73] Assignee: Carl Zeiss Stiftung, Fed. Rep. of Germany

[21] Appl. No.: 948,215

[22] Filed: Oct. 3, 1978

[30] Foreign Application Priority Data

Oct. 5, 1977 [DE] Fed. Rep. of Germany ....... 2744707

[51] Int. Cl.³ .................. A61B 3/14; G02B 21/22
[52] U.S. Cl. .................................. 351/7; 350/35; 351/16
[58] Field of Search .............. 351/7, 6, 16, 13; 354/62; 350/235, 236, 184, 186, 35, 33

[56] References Cited

U.S. PATENT DOCUMENTS

| 3,259,039 | 7/1966 | Ohajima | 351/7 |
| 3,533,342 | 10/1970 | McMillin | 351/7 |
| 3,549,250 | 12/1970 | Pantenburg | 350/184 X |
| 3,915,564 | 10/1975 | Zeiss | 351/7 |
| 4,015,898 | 4/1977 | Shirmer | 351/16 X |

FOREIGN PATENT DOCUMENTS

Z 471714  4/1956  Fed. Rep. of Germany ........... 350/184

Primary Examiner—Paul A. Sacher
Attorney, Agent, or Firm—Stonebraker, Shepard & Stephens

[57] ABSTRACT

An ophthalmological instrument for stereoscopic examination of the fundus or retina of the eye of a patient, and documentation thereof, as by photographing it. The instrument provides an observation light beam path, and an illumination light beam path. In the observation beam path are various optical elements for producing an image of the fundus at appropriate places, and a beam splitter to split the beam into two parts for stereoscopic viewing. A movable deflector can be shifted to a position to deflect at least part of the beam to a camera or other documentation device.

10 Claims, 1 Drawing Figure

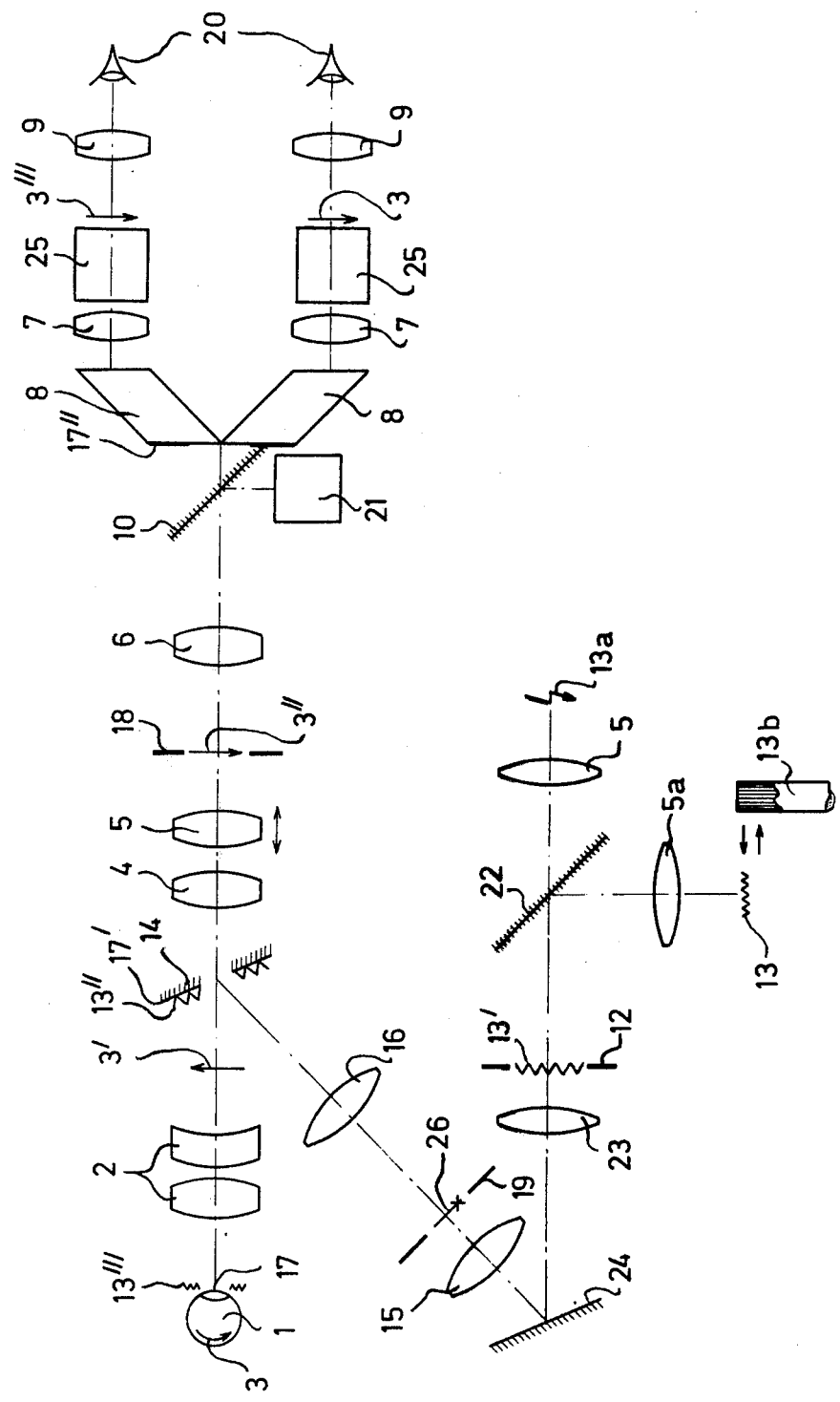

OPHTHALMOLOGICAL INSTRUMENT

This invention relates to an ophthalmological instrument for the stereoscopic examination and documentation of the fundus or retina of the eye, the instrument having an observation beam path and an illumination beam path.

For the examination of the fundus of the eye there are known a number of optical instruments, each of which in part satisfied the requirements for these examinations. Optically expensive instruments which are known under the name of ophthalmoscopes or fundus or retina cameras give, within a field of 30°, a picture of the human retina free of reflections, flattened, and with sufficient power of resolution for direct observation and/or for photographic documentation. The establishing of fluorescence angiograms is also possible with the known instruments. Stereoscopic photographs are possible with the known instruments, but only with the so-called successive method, i.e. the two photographs for a stereo picture are taken in succession. This method has the disadvantage that in connection with the dynamic process of fluorescence angiography not only in each case is half of the time information lost but, in case of possible visual movements of the patient, the entire stereo impression is lost.

There are also known ophthalmological instruments for the examination of the retina which have a larger angle of coverage than 30°, for instance 60° or 100°. These known instruments have the severe disadvantage that they are operable only in direct contact with the cornea and that, due to their large field angle, they give a reduced resolution of details. The handling of these instruments requires great skill. The possibility of joint observation for teaching and discussion purposes is possible in principle in the case of these known instruments, but is scarcely practiced due to reasons of light economy.

The object of the present invention is to provide a new ophthalmological instrument having a maximum field angle of 50° for the examining and photographing of the retina, which instrument is free of the errors and defects of the known instruments while suitably satisfying all requirements of ophthalmological examinations and, in addition, making it possible to carry out scientific research.

Another object consists in combining high comfort of operation with rapidity, and in retaining that which has proven its worth while expanding and improving it.

These objects are achieved in accordance with the invention in the manner that there are arranged in the path of the observation beam, in the direction from the eye of the patient to the observer, a main objective or first lens group for producing an inverted flat image of the fundus of the eye, a second group of lenses for imaging said image at infinity, a third group of lenses for producing a real, erect intermediate image at the locus of a visual field stop provided behind the third group of lenses, and a fourth group of lenses for focusing said intermediate image at infinity. Furthermore, behind the fourth group of lenses there is arranged a beam deflection system which can be engaged in at least two positions, as well as a stereoscopic observation tube. Also means are provided in a known illumination beam path for focusing a light-source image in the plane of a perforated mirror arranged in the path of the observation beam, the main objective producing in the pupil of the patient another image from the light-source image produced in said plane.

SUMMARY OF THE INVENTION

In one advantageous embodiment of the invention, the stereoscopic observation tube contains a prism system for the splitting of the pupil, a pair of objectives, a prism system for image reversion, and a pair of oculars.

In order to compensate for ametropia the third group of lenses of the observation beam path is advisedly axially displaceable.

In order to change the image scale and thus the size of the field angle, a variable focal length is advantageously provided for the fourth group of lenses in the observation beam path. In accordance with the invention, there can be provided for this lens group either different discrete values for the focal length, or continuously variable values. In order to avoid the action of excessive brightness on the fundus when changing the image scale, an illuminating field stop is provided in a plane conjugated to the locus of the first fundus image, the varying mechanism for the fourth lens group being advantageously coupled with the mechanism for the illuminating field stop.

Reference to a "group" of lenses is not intended to imply that the "group" contains more than one lens element. The lens group or component may be made up of a single element or a plurality of elements.

The deflection system provided in front of the stereoscopic observation tube can advisedly be set in an observation position and in a documentation or photographing position. In one suitable embodiment of the invention it consists of a swingable mirror. In the observation position of this swingable mirror, the observation beam path is deflected into the stereoscopic observation tube. In the documentation position of the swinging mirror the observation beam path is deflected to a documentation device, for instance a camera, which contains a pupil splitting system and optical elements for successive and/or simultaneous stereo documentation.

In the plane in the illumination beam path which is conjugated with the first fundus image, reference marks can be provided which are projected onto and appear on the fundas.

The advantages obtained with the invention include the fact that the instrument of the invention represents a building-block system for the observation, joint-observation, and documentation of the image of the fundas, in which connection both stereoscopic observation and simultaneous-stereoscopic documentation of the fundus is possible, with compensation for ametropia and astigmatism, and a simple possibility is provided for varying the field angle. The 50° wide-angle fundus camera in accordance with the invention operates free of contact, with a so-called free-working distance of 50 mm. It can therefore be operated even by semiskilled persons. For the first time, it makes possible a simultaneous fluorescence angiography for both images of a stereo photograph, which affords new possibilities in the diagnosis and treatment, for instance, of diabetic retinopathy.

The optical structure of the instrument of the invention makes possible stereoscopic photo documentation at all times during the stereoscopic observation. This stereoscopic documentation is effected with only one still camera with splitting of format on a single negative or a single slide. In this way assurance is had that the photographic conditions for both photographs are the same and the possibility of a mixup is excluded, which also benefits filing. The monitoring of the course, for instance, of the formation and change of prominences or the exact determination of glaucomatous excavation of the papilla of the optic nerve is for the first time quantitatively possible as a result of the stereoscopic observation and simultaneous-stereo documentation.

The rapid switching from a field angle of 50° to 30° by changing the focal length of a group of lenses in the observation beam path provides assurance that continuous studies which extend back into past years need not be interrupted and acquired impressions and dimensions disturbed. Thus the rapid switching to the different magnifications is a substantial aid in diagnosis, since on the one hand a large field angle indicates the size of a finding and immediately thereupon a detail can be recognized better and documented with higher magnification.

In particular, the advantages of the ophthalmological instrument of the invention include the fact that it combines the stereoscopic observation and documentation of a flat reflex-free image with a 50° fundus field with rapid switching to the known 30° field with a 50 mm. free-working distance to the eye, telecentric beam path, and simultaneous observation, thus expanding the previous standard and without mutual exclusion of individual functions.

BRIEF DESCRIPTION OF THE DRAWING

The single FIGURE is a diagram of the optical structure of the instrument in accordance with a preferred embodiment of the invention.

DETAILED DESCRIPTION

In the observation beam path, behind the eye 1 of the patient with the fundus 3 and the pupil 17, there is a main objective or first lens group 2, a perforated mirror 14, and the further lens groups 4, 5 and 6. Between the lens groups 5 and 6 there is a visual field stop 18. In the case of an emmetropic eye, an image 3' of the fundus is produced at the focal point of the main objective 2. It is focused at infinity by the lens group 4. The following lens group 5 produces a real intermediate image 3" at the locus of the visual field stop 18. The lens group 6 may have different focal lengths, the focal length being variable either in discrete values or continuously. For example, the lens group 6 may have several lenses of different focal lengths mounted on a rotatable turret to bring any selected lens into the observation path, or it may be in the nature of a "zoom" lens assembly. By changing the focal length of this lens group 6, the imaging scale and thus the size of the field angle can be changed. The intermediate image 3" is focused at infinity by the lens group 6.

The fundus is observed via a stereoscopic observation tube which contains a prism system 8 for the splitting of the pupil, objective lenses 7, a prism system 25 for the reversing of the image, and oculars 9. The lens groups 2, 4, 5 and 6 can be used, even decentered, without impairing the quality of the imaging for purposes of stereoscopic observation or documentation, the splitting of the pupil being effected by the prism group 8. For non-stereoscopic observation or documentation the pupil is not split and the lens groups 2, 4, 5 and 6 are used centrally. The field of view of the ocular or the film format is always fully utilized by the beam path, telecentric with respect to the pupil imaging, between the lens groups 5 and 6. The compensation for ametropia is effected by displacing the lens group 5 axially. For purposes of documentation and/or joint observation the beam path is deflected to the documentation device 21 (e.g., a camera) via a deflection element which, in the embodiment shown in the drawing, is developed as a swing mirror 10.

The pupil 17 of the patient is imaged via the main objective 2 into the plane of the perforated mirror 14. The lens groups 4, 5 and 6 produce from this pupil image 17' a further pupil image 17" in the entrance surface of the prism system 8.

In the illumination beam path a source of light such as an incandescent bulb is designated 13, and the exit surface of a light pipe is designated 13b. Either light source may be used as desired. The collector lens 5a serves to image these optionally usable sources of light. By means of the splitting system 22, a flash lamp 13a can optionally be imaged via a collector lens 5. The first image 13' of the source of light appears in the plane 12 of the aperture stop. Via the lens groups 23, 15 and 16 as well as the reflection mirror 24 the first light-source image 13' is focused at 13" in the plane of the perforated mirror 14. The main objective 2 throws the image 13''' of this second light-source image 13" into the pupil 17 of the patient. In a plane which is conjugate to the locus of the first fundus image 3' a limiting of the illuminated field on the fundus can be effected by an illuminating field stop 19 in the illumination beam path. The said plane is suitable also for the provision of reference marks 26 which are to be projected onto and appear on the fundus.

The illumination field stop or diaphragm 19 has an adjustable aperture. Preferably the mechanism for adjusting the aperture is mechanically coupled, by any suitable mechanical linkage, to the mechanism for adjusting the focal length of the fourth lens group 6 so that as this focal length is adjusted (as by turning a turret or swinging an arm which carries two or more lenses of different focal length) the aperture of the stop 19 will be adjusted to a size appropriate to the focal length selected for the lens.

The deflection system 10 may conveniently include a partial transmitting mirror, so that the incoming beam will be partially transmitted through the mirror in one direction and partially reflected by the mirror in another direction, to enable joint observation of the incoming beam by two observers. For this purpose, two separate stereoscopic observation tubes may be provided, for use by two observers. Or again, the partially transmitting mirror may be used so that part of the light beam goes to an observation tube and another part goes simultaneously to the documentation device 21, such as a camera, whereby the picture may be taken simultaneously with the observation.

The light beam passing to the camera or other documentation device preferably contains a pupil splitting system similar to the system 8 in the observation tube, and other optical elements as needed to enable simultaneous taking of stereoscopic pictures.

What is claimed is:

1. Ophthalmological instrument for stereoscopic examination and documentation of the fundus of the eye, said instrument comprising means forming an observation beam path and an illumination beam path, said observation beam path having, successively in a direction from the eye (1) of a patient to be examined toward the eye (20) of an observer, a main objective (2) for producing a first inverted flattened image (3') of the fundus (3), a second lens group (4) for focusing such image (3') at infinity, a third lens group (5) for producing a real erect intermediate image (3") at a locus behind said third lens group, a visual field stop (18) at said locus where said erect intermediate image is produced, a fourth lens group (6) for focusing said intermediate image (3") at infinity, a shiftable beam deflection system (10) located beyond said fourth lens group and having at least two positions, one of which intercepts light coming from said fourth lens group and another of which permits passage of at least a portion of the light coming from said fourth lens group, and a stereoscopic observation tube, said stereoscopic observation tube including pupil splitting means (8) located beyond said deflection system to split a pupil beam, an observation light beam from said fourth lens group entering said stereoscopic observation tube when said beam deflection system is in one position and being deflected so as not to enter said tube when said beam deflection system is in another position, said illumination beam path including a perforated mirror having an opening through which said observation beam passes and also including means for projecting an image of a source of light via said perforated mirror into the pupil of the eye of the patient.

2. The invention defined in claim 1, wherein said stereoscopic observation tube includes a prism system (8) for splitting light incoming along said observation beam path, a pair of objective lenses (7), a prism system (25) for image reversal, and a pair of oculars (9).

3. The invention defined in claim 1, wherein said third lens group (5) is axially displaceable for ametropic compensation.

4. The invention defined in claim 1, further comprising means for varying the focal length of the fourth lens group (6) in order to vary the image scale.

5. The invention defined in claim 4, further comprising an illuminating field stop (19) located in the illumination beam path in a plane which is conjugated to the locus of the first fundus image (3').

6. The invention defined in claim 5, wherein a plurality of lenses of different focal lengths are provided for said fourth lens group (6) and are arranged to be selectively swung into and out of the observation beam path.

7. The invention defined in claim 6, further comprising mechanism for adjusting said field stop (19), mechanism for swinging said lenses of the fourth group (6), and means coupling said mechanisms to each other for joint movement.

8. The invention defined in claim 1, wherein said deflection system (10) can be set in an observation position and in a documentation position.

9. The invention defined in claim 8, wherein said deflection system is partially light transmitting in two directions in order to make possible joint observation by two observers.

10. The invention defined in claim 8, further comprising a pupil splitting system and optical elements for successive and simultaneous stereo documentation located in a beam path produced by the documentation position of said deflection system (10).

* * * * *